United States Patent
Robinson

[11] Patent Number: 5,853,210
[45] Date of Patent: Dec. 29, 1998

[54] PEN AND INSTRUMENT HOLDER FOR PHYSICALLY IMPAIRED HANDS

[76] Inventor: Gale Robinson, 1455 Uthoff, Fenton, Mo. 63026

[21] Appl. No.: 641,640

[22] Filed: May 2, 1996

[51] Int. Cl.[6] ............................. B25B 29/00; A41D 19/00
[52] U.S. Cl. .................................... 294/25; 2/160; 401/7; 623/65
[58] Field of Search ....................... 294/1.1, 25; 401/6–8, 401/48; 15/443; 623/65; 2/160; 224/217–219

[56] References Cited

U.S. PATENT DOCUMENTS

| | | | |
|---|---|---|---|
| 2,294,997 | 9/1942 | Marrion | 2/160 |
| 2,889,160 | 6/1959 | Nelson | 294/25 |
| 3,834,021 | 9/1974 | White et al. | 2994/25 |
| 4,165,896 | 8/1979 | Hunt | 294/25 |
| 4,447,912 | 5/1984 | Morrow | 2/160 |
| 4,602,885 | 7/1986 | Bischoff et al. | 294/25 |
| 4,606,484 | 8/1986 | Winter et al. | 294/25 |
| 4,957,442 | 9/1990 | Prater | 623/65 |
| 5,110,154 | 5/1992 | Street | 294/25 |
| 5,276,922 | 1/1994 | Floyd, Jr. | 2/160 |

*Primary Examiner*—Dean Kramer
*Attorney, Agent, or Firm*—Patrick D. Kelly

[57] ABSTRACT

Devices are disclosed which can make writing and other tasks easier for people with physically impaired hands, such as people suffering from severe rheumatoid arthritis. These devices include a glove with a mounting attachment, for holding the base of a pen, pencil, or other device, affixed to the glove in the vicinity of the palm region. The mounting attachment on the glove is designed to securely hold the base of a device such as a pen or pencil, toothbrush, key holder, kitchen utensil, etc. The base of each insertable device is provided with a fitting designed for insertion and removal by someone with impaired hands, preferably without requiring assistance by another person. Several accommodating devices can be provided with the glove, as part of a complete set. Some of these devices will contain fixed, non-rotating bases, for use with devices such as pencils or pens; others will use bases that can rotate freely about a point or a single axle, or with various other types of constraints. Devices having two interacting components (such as scissors, pliers, and tongs) are also disclosed for use with these gloves.

18 Claims, 3 Drawing Sheets

PEN AND INSTRUMENT HOLDER FOR PHYSICALLY IMPAIRED HANDS

BACKGROUND OF THE INVENTION

This invention is in the field of mechanical devices to assist people whose hands are physically impaired, due to severe arthritis, injury, or other physiological problems.

A substantial number of people suffer from deformations, chronic pain, and other impairments of the hands, due to injuries or various diseases such as rheumatoid or other severe forms of arthritis. Such impairments often render it difficult or impossible for the affected people to hold and write effectively with a pen, pencil, or other writing instrument, and to operate small devices such as scissors, toothbrushes, kitchen utensils (such as knives, forks, stirrers, spatulas, etc.), and the like.

Several types of grasping devices have been created and patented in efforts to provide assistance to people with impaired hands. For example, U.S. Pat. No. 5,383,737 (Urion 1995) involves a device with a shape comparable to a paperweight with a rounded top; it has a low-friction gliding support on the bottom near the rear, and a pen or pencil tip (a stylus) on the bottom near the front. The user wraps his hand around it and moves the entire device, including the stylus.

U.S. Pat. No. 4,917,517 (Ertz 1990) discloses a molded device which holds a pen or pencil, and which is designed so that a hand can be rested on top of it. To write with it, the user glides the device, including the pen or pencil, across a paper surface.

U.S. Pat. No. 3,787,898; (Walker 1974) discloses a glove-type device with a low-friction pad that contacts and rests upon the paper that is being written upon. This low-friction pad is intended to glide across paper smoothly, so that writing takes less effort.

U.S. Pat. No. 4,957,442 (Prater 1990) discloses another glove-type device, which rests on top of a small platform that is supported by a rolling-ball device, comparable to the ball from a roll-on deodorant. A pen or pencil holder is affixed to the movable platform.

All of these devices have been patented; however, to the best of the applicant's knowledge and belief after a diligent search, none of these devices are actually available for sale to the people who need them. The applicant suffers from a serious impairment of her hands, and she made a diligent, sustained effort to locate and obtain any type of device that was available to help her write. She wasn't able to obtain or even locate any such device, so she created her own, and she continued to test and improve it until it worked in the way she wanted and needed. The device that arose out of her efforts became the basis of this invention.

Accordingly, one object of this invention is to provide a device which can help or enable people with physically impaired hands to write, and to write more easily and legibly, using stylus-type instruments such as pens or pencils.

Another object of this invention is to provide a multi-purpose device which can assist or enable people with physically impaired hands to hold and use various hand-held tools and devices (such as toothbrushes, keys, scissors, tongs, and kitchen utensils) with greater ease, comfort, and dexterity.

Another object of this invention is to provide a multi-purpose device which can assist or enable people with physically impaired hands to hold and use hand-held tools (such as tongs or pliers) that can close upon and grip various objects to be manipulated.

These and other objects of the invention will become clear through the following summary, drawings, and description.

SUMMARY OF THE INVENTION

This invention relates to devices that can make writing and other tasks easier for people with physically impaired hands, such as people suffering from severe rheumatoid arthritis. These devices include a glove with a mounting attachment, for holding the base of a pen, pencil, or other device, affixed to the glove in the vicinity of the palm region. The mounting attachment on the glove is designed to securely hold the base of a device such as a pen or pencil, toothbrush, key holder, kitchen utensil, etc. The base of each insertable device is provided with a fitting designed for unassisted insertion and removal by someone with impaired hands. Several accommodating devices will be provided with the glove, as part of a complete set. Some of these devices will contain fixed, non-rotating bases, for use with devices such as pencils or pens; others will use bases that can rotate in a single direction, and still others can use bases that allow free rotation in any direction. Two-component devices such as scissors, pliers, and tongs are also disclosed, for use with these gloves.

DESCRIPTION OF THE PREFERRED EMBODIMENTS

Figure 1:
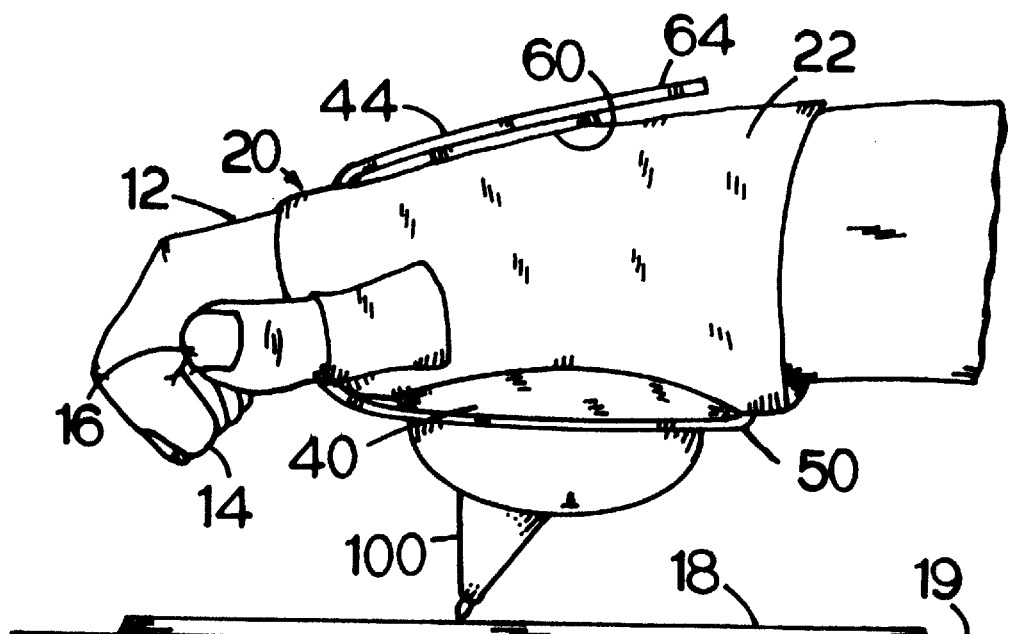
FIG. 1 is a side view of a glove of this invention, in use while writing, with a writing pen extending downward from the palm.

Referring to the drawings by reference numbers, FIG. 1 shows a hand 12 wearing a glove assembly 20 which has a glove component 22 and various other components described below, and having a writing pen 100 temporarily secured to the glove assembly 20 by means of a mounting attachment 40 and attachment straps 50.

The glove component 22 encloses hand 12, which is physically impaired. Without requiring any active involvement or support from fingers 14 or thumb 16, hand 12 is using pen 100 to write on the top sheet of a paper pad 18 that is supported by a desk or table surface 19. The pen 100 provides either full or partial support for the weight of the hand 12, depending on the condition (shape, strength, etc.) of the hand and fingers.

The finger portions 24 of a glove 20 (shown in FIG. 3) can be either partial or complete (enclosed) finger sleeves, depending on the user's preferences, which may depend on factors such as the condition of the user's fingers, and the ambient temperature where the glove will normally be used. For example, a cool and lightweight glove with only partial fingers (or finger straps, which encircle only the base of a finger) may be preferred in warm environments and seasons, while a heavier, warmer glove may be preferred during the winter and in chilly locations. It is anticipated that a typical user will want to own a set of gloves having various different characteristics; some will have fully-enclosed finger sleeves, for use in winter, while others will have only partial finger sleeves, for use in summer. All of these gloves preferably should be adapted to interchangeably accommodate any of the actuator devices described herein. If desired, gloves can be manufactured in small, medium, and large sizes, to maximize proper fit and comfort for different users.

Some users also may prefer gloves with specialized fingertips, to protect the fingertips of the hand from abrasion while writing. Such glove fingertips can be made of smooth-surface molded shallow plastic cups, comparable to shallow thimbles, which can be glued to fabric fingertips; alternately, gliding fingertips can be made of a material that glides easily over smooth surfaces, such as "Gore-Tex" (™; this trademark is used to describe a fabric that contains polytetrafluoroethylene coated onto a durable woven fabric such as nylon).

The term "glove" is used broadly herein, to include standard gloves (with either full or partial finger and thumb enclosures), mitten-type devices, and harness-type hand-covering devices, so long as such hand coverings are designed to fit around a hand in a snug and secure manner during use, while allowing a degree of conformance and comfort (and, where desired, freedom of movement) for the thumb and fingers. Most gloves designed for use herein will cover at least the palm area, and will also comprise either a fabric component to cover the back of the hand, or a network of straps or cords that cross the back of the hand. In addition, most gloves for use as described herein will comprise either finger sleeves for all four fingers (and for the thumb, if desired), or sleeves or ring-type structures for securing a harness-type glove to at least two fingers (as used herein, the term "finger" includes the thumb). For example, a harness-type glove device that is secured to the wrist by a wrist-band, and to the first and fourth fingers by sleeves or rings can be adequate for use as described herein, provided that the mounting attachment is adequately secured to the hand-harness and that the entire subassembly can be fitted onto a physically impaired hand with minimal discomfort and with adequate snugness and stability to allow a desired use as described herein. In general, to provide a snug and secure fit upon a hand, a glove component as described herein must have at least a palm portion, a portion which wraps around the wrist (which may include the heel portion of the hand immediately adjacent to the wrist), and sleeve portions which wrap around at least two fingers.

For convenience, some of the illustrative descriptions below will refer to a pen. It should be understood that any such references apply equally to pencils and other comparable writing instruments. As used herein, "writing instrument" is limited to pens, pencils, felt-tipped or porous-nibbed devices, paint or ink brushes, and other stylus-type or comparable devices that are normally held in a single hand while being used to make marks directly onto paper or other surfaces; this term excludes typewriters, printers, or other more complex devices that might be regarded as "writing instruments" under broader definitions.

In the claims, the term "actuator component" is used to describe a writing device, toothbrush holder, key holder, or any other device that is temporarily secured in the mounting attachment 40 of a glove 20 so that it can be manipulated by the user. For example, in FIG. 1, pen 100 serves as the actuator component. A complete glove-and-actuator assembly which is ready for use comprises two subassemblies: a glove assembly 20, and an actuator subassembly 100. These are temporarily coupled to each other, to form a complete assembly which functions in the desired manner.

Figures 2, 3:
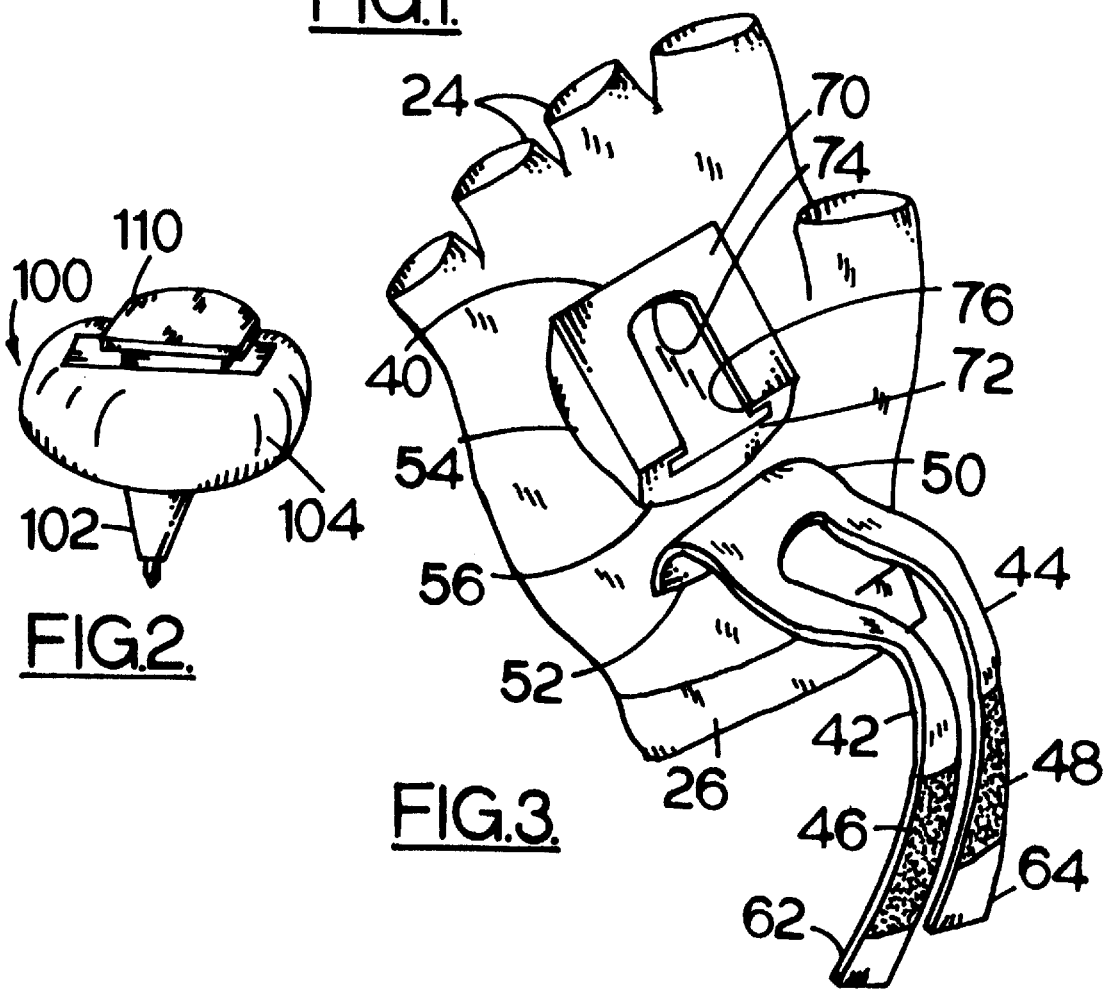
FIG. 2 is a perspective view of a pen, with a squat elliptical barrel to hold a substantial quantity of ink, and a molded plastic fitting on the back of the barrel, for insertion into a mounting attachment on a glove.
FIG. 3 is a perspective view of the palm side of a glove, showing a molded mounting attachment in the palm of the glove, and securing straps attached to the heel or wrist area of the palm.

An elastic or adjustable wristband 26, as shown in FIG. 3, can be provided as part of a glove 20 if desired, but a preferable design, which provides a snug, secure fit without using a narrow wristband that might need to be wrapped tightly around the wrist, can be designed in a manner comparable to a golf or batting glove. This design provides an oversized flap covering a large portion of the back of the hand, rather than a narrow wristband. The oversized flap can be covered, on one side, with hook or loop fabric commonly referred to as VELCRO. This flap can be pressed and secured against a pad of accommodating loop or hook material which is permanently affixed to the glove material on the back of the hand.

As shown in FIG. 2, pen device 100 (or any other actuator device) is provided with an attachment coupling 110 on the side that will be placed against the palm of the hand. Pen device 100. also comprises a stylus portion 102, and an ink barrel 104 which in the example shown has a relatively flattened, squat, elliptical configuration, to allow it to contain a substantial quantity of ink while minimizing its length, and maximizing ease and comfort of use. Attachment coupling 110 is designed to be inserted into and secured within the mounting attachment 40 in glove assembly 20.

Pen 100 is designed to be relatively short, such as about 4 to 6 cm long (about 1.5 to 2.5 inches). This allows the hand to ride comfortably on top of it as the stylus 102 presses against and writes upon a sheet of paper 18, as shown in FIG. 1. In general, ball-point pens are preferable to fountain pens for such use, since several pounds of weight may be resting upon the tip of stylus 102 as it writes.

Mounting attachment 40 is securely affixed to the palm region of glove 20, by means such as glue, or by stitches, rivets, or screws which pass through the material on the palm of glove 20. The mounting attachment 40 can take any of several configurations, so long as it is designed to allow unassisted insertion and removal of pens, pencils, and other devices by an owner/operator whose hands are seriously impaired but not totally immobile. This will maximize the utility of these devices for most people who need them, and it will also allow them to be of great utility to those who need help from others when emplacing or removing either a glove or an actuator. The overriding goal of this invention is to facilitate various types of chores, such as writing and the use of devices such as toothbrushes and kitchen utensils, for people with a wide range of impairments in their hands.

Accordingly, the mounting attachment 40 shown in FIG. 3 interacts with at least one strap which helps secure the actuator device in place. In a preferred embodiment, the mounting attachment 40 interacts with two straps 42 and 44, which are positioned so that they will secure two opposed sides of the base of the actuator device, thereby "flanking" the actuator device and securing both of its sides while it is in use.

Preferably, the two straps 42 ad 44 should have securing components 46 and 48 positioned near the ends of straps 42 and 44. Preferably, as shown in FIG. 3, securing components 46 and 48 should not be positioned at the very ends of straps 42 and 44; this will allow short segments 62 and 64 of free-hanging material to remain at the ends of the straps; this will make the straps 42 and 44 easier to work with while being secured or detached. Securing components 46 and 48 can be made of either the hook portion or the loop portion of "hook-and-loop" fabric (commonly known by the trademark "VELCRO").

The straps 42 and 44 can create or be attached to the ends of a U-shaped flap 50. The base of flap 50 is permanently secured to the palm of glove 20 by a line of stitching 52. In a preferred orientation, the flap stitching 52 is positioned near the heel of the hand, on the palm side on the glove 20, and the straps 42 and 44 extend toward (and preferably through) the gaps between the finger sleeves 24. In one embodiment, the straps 42 and 44 can comprise relatively narrow cords, made of nylon or other suitably strong stranded or narrow material which can pass comfortably between adjacent fingers.

This design will allow the VELCRO attachment areas 46 and 48 near the ends of straps 42 and 44 to be secured to either one large or two small accommodating loop or hook pads 60, mounted on the back side of glove 20 as shown in FIG. 1. This configuration also allows a short segment (such as about 2≧3 cm, or 1 inch) of excess material 62 and 64, at the end of each strap 42 and 44, to extend beyond the VELCRO attachment pad(s) 60 on the back of glove 20. Alternately, this configuration can allow a molded or curled plastic gripping device to extend in an upward direction, away from the back of the hand. Either configuration (or both, used together) can make it easier for users with impaired hands to secure and detach the straps when a pen or other device needs to be inserted into or removed from the mounting attachment 40, while also preventing the loose ends from getting in the way of the pen or other device while it is in use, below the palm of the hand.

For additional comfort, the back side of mounting attachment 40 preferably should be rounded, as indicated by edges 54 and 56. This will avoid or minimize and hard and potentially abrasive square edges. If desired, mounting attachments can be made in different sizes, or they can be molded to fit individual hands.

FIG. 3 also depicts a receptacle 70 which secures an accommodating base of an actuator device. Receptacle 70 includes a first open end 72, an opposed closed end 74, and two guide rails 76.

Pen 100 or any other actuator device can be secured in glove 20 by a straightforward series of steps, comprising (1) detaching the VELCRO securing portions 46 and 48 of straps 42 and 44 from the attachment pad(s) 60 on the glove; (2) unwrapping the straps 42 and 44 from between the fingers and pulling the straps away from the palm of the glove 20; (3) sliding attachment coupling 110, on the base of device 100, into mounting attachment 40 on glove 20; (4) securing flap 50 and straps 42 and 44 over the device 100, either by placing them next to and flanking the attachment coupling 110 (as shown in FIG. 1) or by placing them across ink barrel 104, depending on its size and shape. The straps are placed between adjacent fingers, and the securing components 46 and 48 are pressed against attachment pad(s) 60 on the back of the glove.

When device 100 is no longer needed, it can be detached and removed from glove 20 by detaching the straps 42 and 44 from the attachment pad(s) 60 on the back of glove 20, pulling the straps out from between the fingers and away from the palm of glove 20, and removing device 100 from the palm of the glove 20 by sliding attachment coupling 110 on device 100 out of the mounting attachment 40.

In an alternate preferred embodiment, glove 20 does not need to be provided with a molded plastic mounting attachment 40, if the devices which are designed for use with the glove have bases which are designed to be secured adequately merely by placement of the straps 42 and 44. A molded plastic mounting attachment 40 can provide a high level of security and immovability, and can prevent any rotation of a device 100 which is secured in it; however, this level of control is not necessary for all uses or for all users, and a simpler, less expensive system may be adequate for many users, which eliminates both the mounting attachment 40 in glove 20 and the need for a special attachment coupling 110 on device 100.

Some users who have a degree of residual functioning in their fingers will be able to use devices, such as pen or pencil holders which can accommodate conventional pens or pencils and which will position a pen or pencil between two fingers, or between the thumb and first finger. These types of devices, positioned between the fingers, can be provided by either of two designs. In one design, a glove as shown in FIG. 3, with a mounting attachment 40 centered in the palm, can be used with an accommodating device that extends up toward the finger portion of the glove. In a second design, the mounting attachment 40 can be moved to a different position, up closer to the finger region of the glove. Preferably, both of these sets of devices should be made available, and users who want both types can obtain them.

Figure 4:
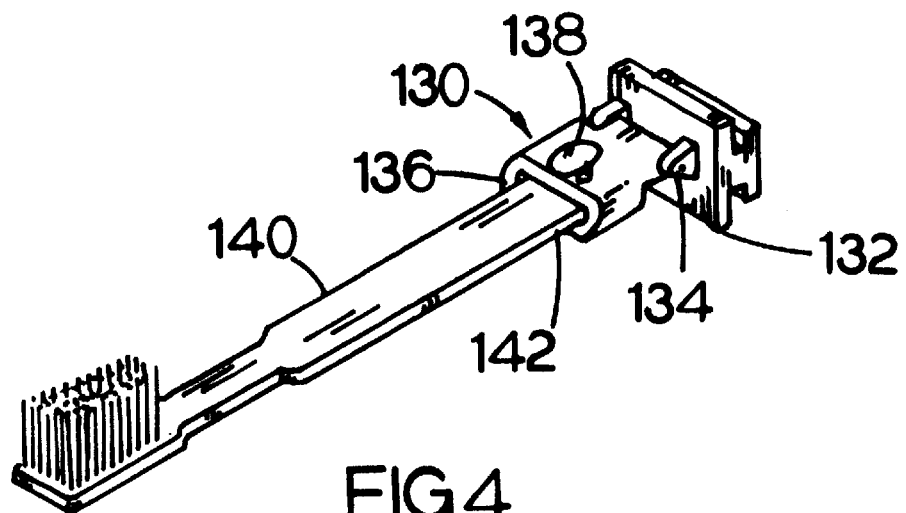
FIG. 4 is a perspective view of a toothbrush holder device, with a base that provides a hinge which allows rotation about a single axle.

FIG. 4 depicts a device 130 with a base 132 that provides a rotatable hinge or axle 134. This allows rotation of an instrument or other device (such as toothbrush 140, shown in FIG. 4) about an axle which remains close to the palm of the user. One end 142 of the handle of toothbrush 140 is pressed into a gripping device 136. The toothbrush is securely gripped in the gripping device 136 by suitable means, such as convoluted rubber inner surfaces (not shown) or by a clamping mechanism, such as a threaded screw 138 which passes through one side of the gripping device 136, as shown.

If desired, an instrument-holding device comparable to device 130 can also be provided any other type of useful mechanism. One example is a rotatable device that allows an instrument such as a toothbrush to be rotated in secure 90° increments. This will make it easier for a user to turn an instrument such as a toothbrush in any desired direction, while it holding the toothbrush securely in the desired direction until the user wants to rotate it another 90°.

Figure 5:
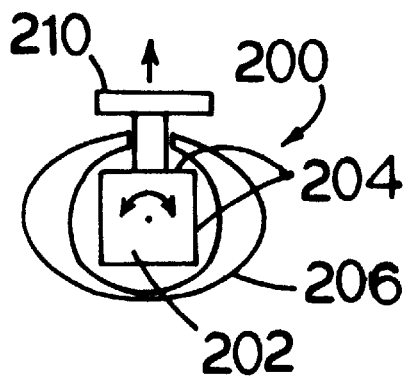
FIG. 5 is a cross-sectional cutaway view of a device that allows constrained rotation of a square-faceted axle inside an enclosing sleeve, if a constraining device is pulled away during rotation.

Mechanisms which allow constrained rotation (or nearly any other type of controllable movement) can be provided in any of numerous ways known to those skilled in the art. One example of a constrained rotation device 200, shown in a cutaway view in FIG. 5, shows a rotatable axle 202 with squared facets 204. The square-faced axle 202 can rotate within a sleeve 206, but only if a constraining device 210 (which can be spring-mounted, slidably engaged in a slot, etc.) is temporarily pulled away from the axle 202 so that it does not press against one of the facets 204. Alternately, various other devices (including double-cylinder devices, comparable to the rotating internal cylinder mechanism used in most retractable ball-point pens) can also be adapted for use as described herein.

Figure 6:
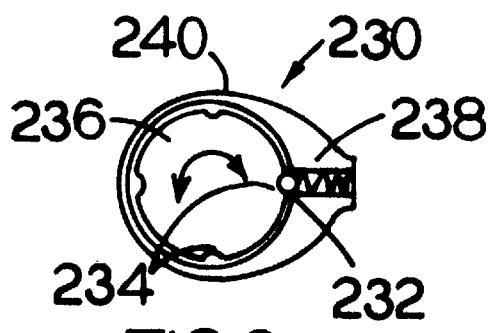
FIG. 6 is a cross-sectional cutaway view of a device that allows rotation of an axle inside an enclosing sleeve, using a spring-loaded detente which can interact with any of four indentations in the axle.

Another device that can provide constrained rotation, shown in FIG. 6, uses a "detente" device 230, in which a ball 232 or comparable finger-type device fits into an indentation 234 in a rotating axle 236. The ball 232 is pressed into the indentation 234 by the force of a compressed spring 238, which is held in place by an enclosure device 240. If the twisting force being imposed on axle 236 exceeds a certain threshold level, the spring 238 will be further compressed, the ball 232 will be forced out of the indentation 234, and the axle 236 will rotate until the next indentation reaches the detente position, where it will engage the ball 232. This engagement will prevent further rotation until the twisting force on axle 236 again exceeds the threshold level.

Figure 7:
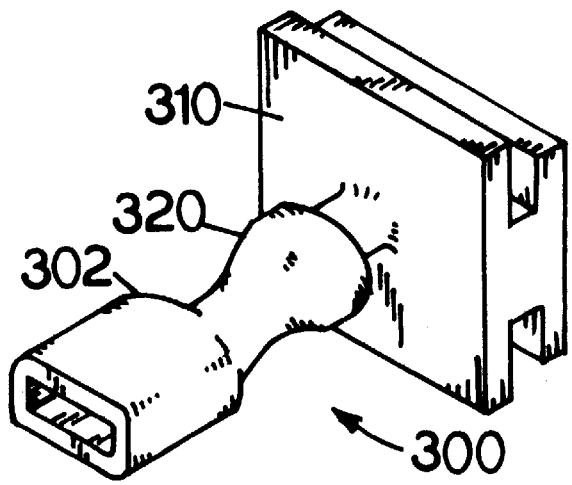
FIG. 7 is a perspective view of a gripping device with a base having a ball attachment which allows free rotation of a gripping device in any direction relative to the base.

In another alternate preferred embodiment, FIG. 7 shows a device 300 which allows free rotation of a holding device 302 in any direction relative to base 310. This can be provided by a ball-type device 320 (comparable to the ball in a roll-on deodorant applicator; also see U.S. Pat. No. 4,957,442, by Prater), by a dual-hinge device (not shown) with two axles that are angled with respect to each other, in a manner comparable to a gimbal mounting.

Figure 8:
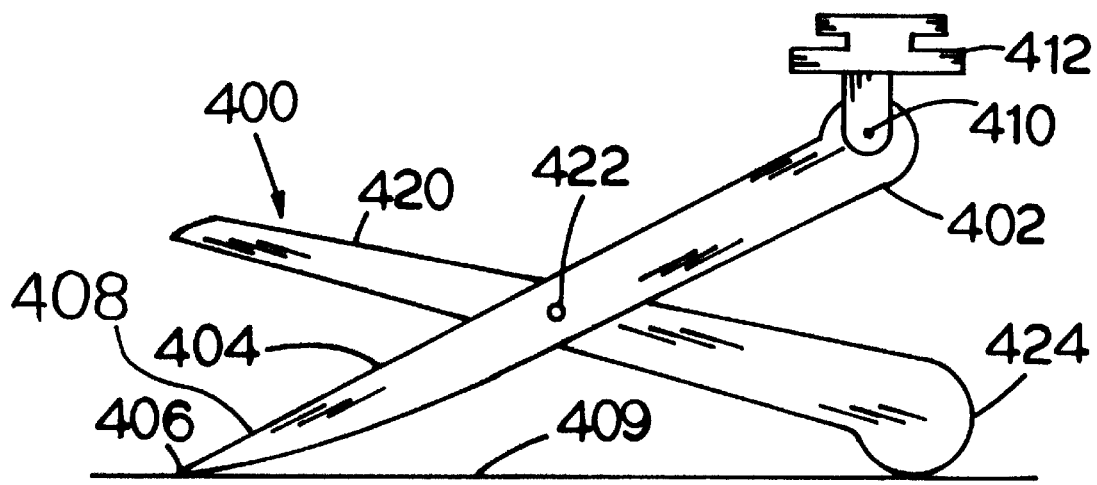
FIG. 8 is a perspective view of a scissors device attached to a base that can be inserted into a mounting attachment on a glove, allowing the scissors to be operated by alternately raising and lowering the hand while the scissors rest on a supporting surface.

In another alternate preferred embodiment, a device or instrument having two movable interacting components (such as the two blades in a pair of scissors, or the two components in a pair of tongs or pliers) can be provided, as shown in FIG. 8. In this embodiment, which shows a pair of scissors 400 for use by someone with impaired hands, the handle end 402 of first blade 404 is coupled directly to an accommodating glove, via a rotatable axle 410 which is coupled to glove attachment coupling 412. The tip 406 of the cutting portion 408 of blade 404 will rest and ride upon the surface 409 of a table, desk, or other supporting structure while the scissors 400 are in use. The tip 406 of blade 404 can have a conventional sharp tip if desired; alternately, it can be provided with a flattened tip with a rounded or chisel-surfaced leading edge, to ensure that it will ride smoothly across a table surface while minimizing undesired poking, jabbing, or tearing.

The second blade 420 is coupled to the first blade via a pivot or axle 422; as in conventional scissors, the blades can rotate relative to each other, using pivot 422. The handle end 424 of second blade 420 will ride upon the surface 409 of the table or desk, and can be provided with extra weight to ensure that it continues to ride or rest on surface 409.

Each time the glove is lowered by the person using the scissors 400, the scissor blades 404 and 420 will close together, cutting through any paper, cloth, or other suitable material that has been placed between then. Each time the glove is raised, the blades will open again. By alternating these lifting and lowering motions, and coupling them with a forward motion when necessary, the scissor blades will alternately open and close, allowing the user to cut through any paper, cloth, or other material that he or she desires to cut.

Figure 9:
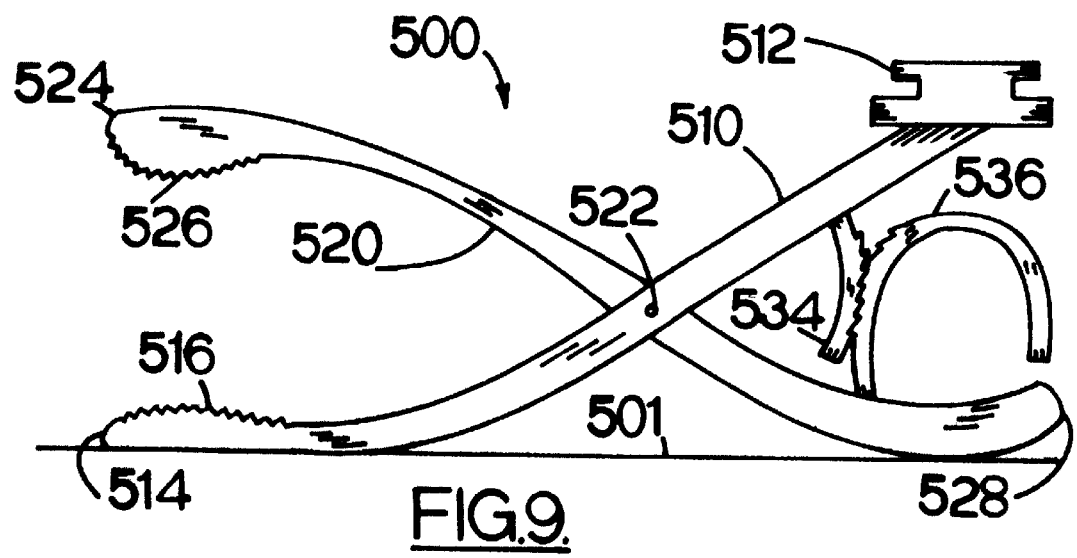
FIG. 9 is a perspective view of tongs or pliers for gripping an item, with a ratcheting mechanism that allows the jaws of the tongs or pliers to remain closed around an object which has been secured in its grasp.

In another alternate preferred embodiment, a grabbing or gripping device 500 which functions as a pair of tongs or pliers is shown in FIG. 9. In this device, first component 510 (which can be called a handle, blade, prong, or any other suitable name) is coupled directly to a glove attachment coupling 512. To maximize solid gripping and firm control of an object gripped by this device, this attachment point preferably should be fixed rather than rotating. The gripping end 514 (also called the jaw end) of component 510, which rides on desk or table surface 501, can be provided with a ridged, gnarled, or other irregular surface 516 for better gripping traction. In some gripping devices, this surface should be metallic, for strength and durability, while in other gripping devices, it can be coated with rubber, for non-abrasive handling of objects that might be scratched by a metal surface.

The second component 520 is coupled to component 510 via a pivot or axle 522. It comprises a gripping (jaw) end 524 with a ridged or gnarled surface 526, and a handle end 528 which rests on surface 501.

If desired, device 500 can also be provided with a latching device, such as prongs 534 and 536, which have ratcheting sawtooth surfaces on their contacting sides. The extension of prong 536 will assist in disengaging it from prong 534. For times when latching activity is not desired, a mechanism can be provided for moving either prong out of engaging alignment with the other prong; alternately, a similar gripping device with no latching prongs can be provided, as part of a complete set of tools for someone with impaired hands.

Depending on the condition and motility of a user's hands, he or she is likely to have different preferences for different types of devices disclosed herein. For example, when using a device such as a key or knife, some users may prefer to have a keyholder affixed to an immovable base that cannot rotate in any direction, while other users might prefer to have a keyholder or knifeholder that can rotate about a single axle, as provided by the type of device shown in FIG. 4.

In addition, various other mechanical devices can be incorporated into the bases described herein, such as spring-mounted devices, and cushioned devices (using rubber or dry foam, encapsulated gels, sealed air bladders, or any other suitable cushioning device or material).

It is anticipated that a variety of gloves and holding devices can be sold both individually, and in a complete set, comparable to a set of socket wrenches with multiple sockets that can be used interchangeably with two or more socket handles.

In summary, this invention comprises a device for assisting a person with a physically impaired hand, comprising a glove component and at least one actuator component. A plurality of different, detachable actuator devices preferably should be provided, for interchangeable use with one or more gloves. The glove component (which can be a conventional glove with full fingers, a glove with truncated finger sleeves, or any other suitable hand harness) provides a snug, secure, relatively immovable fit upon the hand, when in use. The phrase "relatively immovable", as used herein, refers to a degree of snugness and security which will allow a user to write in clear and legible handwriting if the hand is moved properly, without requiring any movement by any individual fingers or the thumb.

The glove component is provided with a mounting attachment for temporarily coupling an actuator component to the glove in a secure manner during use. To provide maximum stability and control, the actuator component is provided with a base that has a molded attachment coupling which slides into and a mounting attachment affixed to the glove. When coupled together and in proper use, movement of a user's hand will cause a desired movement of the glove and, through it, the actuator component. This will allow the person to write (if the actuator device is a pen or pencil), or to carry out other useful functions, with other types of devices and instruments, such as toothbrushes, keys, kitchen utensils, scissors, tongs, etc.

Thus, there has been shown and described a new and useful device for assisting people with physically impaired hands. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

I claim:

1. An article of manufacture for assisting a person with a physically impaired hand, comprising:
    (a) a glove component having a palm portion, a portion which wraps around a wrist, and sleeve portions which wrap around at least two fingers, whereby the glove component fits securely upon the hand while in use;
    (b) a mounting attachment which is permanently affixed to the palm portion of the glove component, comprising a coupling device having a receptacle which comprises (i) a first open end which allows entry of an accommodating actuator base into the receptacle; (ii) an opposed closed end which serves as a securing seat to hold the actuator base in an immovable manner in the receptacle during use of an actuator device; and (iii) at least one rail component to guide the actuator base into a seated position in the receptacle, wherein the coupling device also comprises means for reversibly securing the actuator base in an immovable seated position in the receptacle during use of the actuator device by a person wearing the glove component; and,
    (c) an actuator device having a base and an actuator component, wherein the base is designed (i) to enter the receptacle of the mounting attachment, (ii) to remain in an immovable seated position in said receptacle while the actuator device is being used by a person having a physically impaired hand, and (iii) to be disengaged and removed from the receptacle by the person having the physically impaired hand, after completion of a desired task.

2. The article of claim 1, wherein the glove component, mounting attachment, and actuator device interact with each other in a manner that allows the actuator device to perform a useful task without requiring-any motion by any fingers of the person wearing the glove component.

3. The article of claim 1, wherein the actuator device comprises a writing instrument which has a total length of about 8 cm (3 inches) or less, including the base.

4. The article of claim 1, wherein the actuator device comprises a gripping device which is designed to securely grip one end of a device selected from the group consisting of keys, toothbrushes, and kitchen utensils.

5. The article of claim 1, wherein the actuator device comprises a component which allows rotation of a task-performing actuator component relative to the actuator base.

6. The article of claim 1, wherein the glove component comprises at least one strap having a first affixed end and at least one second detachable end, wherein the affixed end is affixed to the glove at a location proximate to the mounting attachment, and wherein the strap has a length that allows it to be placed across at least a portion of the base of an actuator device before the detachable second end is secured to the glove, thereby allowing the strap to help secure the actuator device to the glove while the actuator device is in use.

7. The article of claim 6, wherein the glove component comprises two straps, positioned so that they will secure two opposed sides of the base of the actuator device while the actuator device is in use.

8. The article of claim 6, wherein at least one strap has a length sufficient to allow the strap to be pulled between two adjacent fingers and then secured, using a detachable end, to an attachment device which is affixed to the glove component and positioned adjacent to the back of the hand while in use.

9. An article of manufacture for assisting a person with a physically impaired hand, comprising:
    (a) a glove component which fits securely around a physically impaired hand and which has a palm portion that covers at least a portion of a person's palm while in use, and which has at least one strap having a first affixed end and a second detachable end, wherein the first affixed end of the strap is affixed to the glove at a location proximate to a mounting attachment which can secure a base of an actuator device in a manner which is immovable during use and reversible after use, and wherein the strap has a length that allows it to be placed across at least a portion of the base of an actuator device before the detachable end is secured to the glove, thereby allowing the strap to secure the base of the actuator device to the glove while the actuator device is in use;
    (b) a mounting attachment which is permanently affixed to the palm portion of the glove component, comprising a coupling device having a receptacle which comprises (i) a first open end which allows entry of an accommodating actuator base into the receptacle; (ii) an opposed closed end which serves as a securing seat to hold the actuator base in an immovable manner in the receptacle during use of an actuator device; and (iii) at least one rail component to guide the actuator base into a seated position in the receptacle; and,
    (c) an actuator device having a base at a first end which accommodatingly interacts with the receptacle of the mounting attachment, and a task-performing component at a second opposed end.

10. The article of claim 9, wherein the actuator device interacts with the glove component in a manner which allows the actuator device to be temporarily affixed to the glove in an immovable manner while the actuator device is in use to perform a desired task, and which also allows a person wearing the glove component on a physically impaired hand to remove the actuator device from the glove component after the desired task has been completed.

11. The article of claim 9, wherein the glove component, mounting attachment, and actuator device interact with each other in a manner that allows the actuator device to perform a useful task without requiring any motion by any fingers of the person wearing the glove component.

12. The article of claim 9, wherein the actuator device comprises a writing instrument which has a total length of about 8 cm (3 inches) or less, including the base.

13. The article of claim 9, wherein the actuator device comprises a gripping device which is designed to securely grip one end of a device selected from the group consisting of keys, toothbrushes, and kitchen utensils.

14. The article of claim 9, wherein the actuator device comprises a component which allows rotation of the task-performing component relative to the base.

15. An article of manufacture for assisting a person with a physically impaired hand, comprising:

(a) a glove component having a palm portion, a portion which wraps around a wrist, and sleeve portions which wrap around at least two fingers, whereby these portions of the glove are designed to fit upon and interact with a physically impaired hand, to provide a snug and secure fit upon the hand when in use by a person wearing the glove component;

(b) a mounting attachment which is permanently affixed to the palm portion of the glove component, comprising a coupling device having a receptacle which comprises (i) a first open end which allows entry of an accommodating actuator base into the receptacle; (ii) an opposed closed end which serves as a securing seat to hold the actuator base in an immovable manner in the receptacle during use of an actuator device; and (iii) at least one rail component to guide the actuator base into a seated position in the receptacle; and, (c) an actuator device having (i) a base which accommodatingly interacts with the receptacle of the mounting attachment; and (ii) a task-performing assembly comprising at least two components which must move with respect to each other in order to carry out a desired task.

16. The article of claim 15, wherein the actuator device comprises scissors having two blades coupled to each other by a pivot.

17. The article of claim 15, wherein the actuator device comprises pliers having two gripping handles coupled to each other by a pivot.

18. The article of claim 15, wherein the actuator device comprises tongs having two gripping handles coupled to each other by a pivot.

* * * * *